US006297378B1

(12) United States Patent
Gupta et al.

(10) Patent No.: US 6,297,378 B1
(45) Date of Patent: Oct. 2, 2001

(54) PROCESS FOR MAKING 2-(2-HYDROXY-4-ALKOXYPHENYL)-4,6-BISARYL-1,3,5-TRIAZINES

(75) Inventors: Ram B. Gupta, Stamford; Dennis J. Jakiela, Orange; Sampath Venimadhavan; Russell C. Cappadona, both of Norwalk; Venkatrao K. Pai, Stamford, all of CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/389,067

(22) Filed: Sep. 2, 1999

Related U.S. Application Data

(60) Provisional application No. 60/099,305, filed on Sep. 4, 1998.

(51) Int. Cl.[7] .................. C07D 251/16; C07D 251/24
(52) U.S. Cl. ................................................ 544/216
(58) Field of Search ............................................... 544/216

(56) References Cited

U.S. PATENT DOCUMENTS

| | | | | |
|---|---|---|---|---|
| 3,118,887 | * | 1/1964 | Hardy et al. ............. | 260/248 |
| 3,244,708 | * | 4/1966 | Duennenberger et al. .......... | 260/248 |
| 3,268,474 | | 8/1966 | Hardy et al. ............. | 260/248 |
| 5,084,570 | * | 1/1992 | Burdeska et al. ............. | 544/216 |
| 5,106,972 | | 4/1992 | Burdeska et al. ............. | 544/219 |
| 5,726,310 | * | 3/1998 | Orban et al. ............. | 544/216 |

FOREIGN PATENT DOCUMENTS

| | | |
|---|---|---|
| 779280 | 6/1997 | (EP) . |
| 884802 | 12/1961 | (GB) . |
| 09-059263 | 4/1997 | (JP) . |

OTHER PUBLICATIONS

Brunetti, H.; Luethi, C. E. *Helv. Chimica, Acta*, 55, (1972) 1566–1595.
Tanimoto, S.; Yamagata, M., *Senyro to Yakahin*, 40, (1995) 339ff.
Horikoshi, Y. et al., *Nippon Kagaku Kaishi*, 3, (1974) 530–535.

* cited by examiner

*Primary Examiner*—Richard L. Raymond
*Assistant Examiner*—Ventataraman Balasubramanian
(74) *Attorney, Agent, or Firm*—Pennie & Edmonds LLP

(57) ABSTRACT

The invention relates to a novel process for making 2-(2-hydroxy-4-alkoxyphenyl)-4,6-bisaryl-1,3,5-triazine and 2-(2,4-dialkoxyphenyl)-4,6-bisaryl-1,3,5-triazine compounds directly from 2-chloro-4,6-bisaryl-1,3,5-triazine compounds with 3-alkoxyphenol, 1,3-dialkoxylbenzene compounds or mixtures thereof. The reaction step to prepare 2-chloro-4,6-bisaryl-1,3,5-triazines from the reaction of cyanuric chloride with substituted aromatic compounds can be combined with the addition reaction of 3-alkoxyphenol or 1,3-dialkoxylbenzene in a two-step, one-pot process. The 2-(2-hydroxyl-4-alkoxyphenyl)-4,6-bisaryl-1,3,5-triazine, and 2-(2,4-dialkoxyphenyl)-4,6-bisaryl-1,3,5-triazine compounds, are useful to stabilize materials against damage by light, heat, and oxygen, and as stabilizers for organic material, or mixtures thereof.

12 Claims, No Drawings

PROCESS FOR MAKING 2-(2-HYDROXY-4-ALKOXYPHENYL)-4,6-BISARYL-1,3,5-TRIAZINES

This application claims benefit from U.S. Provisional Application No. 60/099,305 filed on Sep. 4, 1998.

FIELD OF THE INVENTION

The invention relates to a novel process for making 2-(2-hydroxy-4-alkoxyphenyl)-4,6-bisaryl-1,3,5-triazine and 2-(2,4-dialkoxyphenyl)-4,6-bisaryl-1,3,5-triazine compounds directly from 2-chloro-4,6-bisaryl-1,3,5-triazine compounds with 3-alkoxyphenol, 1,3-dialkoxylbenzene compounds or mixtures thereof. The reaction step to prepare 2-chloro-4,6-bisaryl-1,3,5-triazines from the reaction of cyanuric chloride with substituted aromatic compounds can be combined with the addition reaction of 3-alkoxyphenol or 1,3-dialkoxylbenzene in a two-step, one-pot process. The 2-(2-hydroxyl-4-alkoxyphenyl)-4,6-bisaryl-1,3,5-triazine, and 2-(2,4-dialkoxyphenyl)-4,6-bisaryl-1,3,5-triazine compounds, are useful to stabilize materials against damage by light, heat, and oxygen, and as stabilizers for organic material, or mixtures thereof.

BACKGROUND OF THE INVENTION

Although exposure to sunlight and other sources of ultraviolet ("UV") radiation can cause embrittlement and yellowing of some polymers, this polymer degradation may be inhibited by mixing or coating susceptible polymers with compounds know as UV stabilizers.

Trisaryltriazine compounds are particularly effective UV stabilizers. Triazine UV absorbers are a class of compounds which have at least one 2-hydroxyphenyl substituent on the 2-, 4-, and 6-positions of a 1,3,5-triazine ring. See Formula I.

Formula I

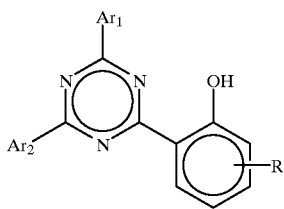

wherein Ar$_1$ and Ar$_2$ are aryl or substituted aryl, and R indicates any type of substitution about the 2-hydroxyphenyl. The Ar$_1$ and Ar$_2$ aromatic rings may contain other substituents or can be fused polyaromatics.

Formula II

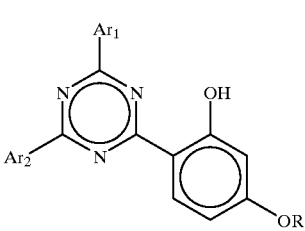

A preferred class of trisaryltriazine UVAs are based on 2-(2,4-dihydroxyphenyl)-4,6-bisaryl-1,3,5-triazines, i.e., compounds where there are two non-phenolic aromatic groups and one phenolic aromatic group derived from resorcinol. See Formula II. Of this class of compounds there are a number of commercial products in which the para-hydroxyl group of the phenolic ring is functionalized and the non-phenolic aromatic rings are either unsubstituted phenyl (e.g., TINUVIN 1577) or m-xylyl (e.g., CYASORB UV-1164, CYASORB UV-1164L, and TINUVIN 400). These 2-(2-hydroxy-4-alkoxyphenyl)-4,6-bisaryl-1,3,5-triazines UV absorbers exhibit high inherent light stability and permanence as compared to other classes of UV absorbers such as benzotriazoles and benzophenones.

SCHEME I

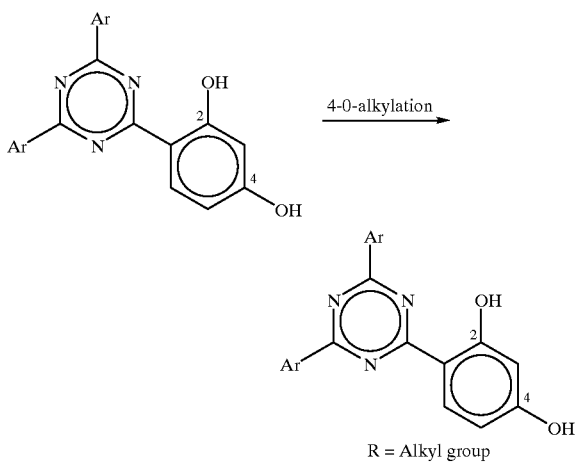

R = Alkyl group

These compounds are generally made by alkylating the corresponding 4-hydroxy precursor, viz., 2-(2,4-dihydroxyphen yl)-4,6-bisaryl-1,3,5-triazine with alkylating reagents. For example, CYASORB UV-1164 is made by reacting 2- (2, 4-dihydroxyphenyl)-4,6-bis (2, 4-dimethyphenyl) -1,3,5-triazine with 1-octyl halide in the presence of a base. See Scheme I. For a review of the previously known methods for making triazine UVAs, see the following articles: (1) H. Brunetti and C. E. Luethi, *Helvetica Chimica Acta*, Vol. 55, 1972, pages 1566–1595; (2) S. Tanimoto and M. Yamagata, *Senryo to Yakahin*, Vol. 40(12), 1995, pages 325–339.

U.S. Pat. No. 3,268,474 to Hardy, et al. describes the formation of 2,4-dihydroxyphenyl-triazine compounds from the reaction of cyanuric chloride with resorcinol derivatives. Tris-aryl-triazines compounds are prepared from the trimerization of substituted aryl amides or aryl nitriles, or the reaction of a cyanuric halide with dialkylated resorcinol. As an example of the latter, cyanuric chloride is allowed to react with excess 1,3-dimethoxybenzene producing a mixture of 2,4,6-tris(2,4-dimethoxyphenyl)-1,3,5-triazine and 2,4-bis (2-hydroxy-4-methoxyphenyl)-6-(2,4-30 dimethoxyphenyl)-1,3,5-triazine compounds.

British Patent Specification 884,802 discloses a method to produce m-xylene substituted mono- or dichlorotriazines from cyanuric acid, m-xylene, and AlCl$_3$.

European Patent Application 0779280 discloses a method of making 2-(2,4-dihydroxyphenyl)-4,6-bis( 2,4-dimethylphenyl)-s-triazine from cyanuric chloride, m-xylene, and resorcinol in a one pot process.

U.S. Pat. No. 3,244,708 discloses a method to produce ether substituted aryl triazines from resorcinol substituted triazines wherein a base deprotonates the phenolic proton prior to addition of an alkylhalide.

U.S. Pat. No. 5,726,310 to Orban et al. discloses an one pot method of making 2-(2,4-dihydroxyphenyl)-4,6-bis(2,4- dimethylphenyl)-s-10 triazine by reacting cyanuric chloride with m-xylene in the presence of a Lewis acid to produce intermediate 2-chloro-4,6-bis(2,4-dimethylphenyl)-s-triazine followed by reaction with resorcinol.

U.S. Pat. Nos. 5,084,570 and 5,106,972 to Burdeska et al. disclose a process for the preparation of 2-(2,4-dihydroxyphenyl)-4,6-diaryl-s-triazines from an intermediate 2-methylthio-4,6-diaryl-s-triazine.

Reaction of cyanuric chloride with phenols formation of either C-alkylation or 0-alkylation has been reported depending on the phenol substituents. Y. Horikoshi et al., *NipDon Kaaaku Kaishi*, 3, (1974) 530–535; CA 81:152177.

More recently Japanese Patent JP 09-059263 discloses a process to make 2-(2,4-dihydroxyphenyl)-4,6-bisaryl-1,3,5-triazine compounds from reaction of 2-oxyaryl-25 4,6-bisaryl-1,3,5-triazine compounds with resorcinol and $AlCl_3$.

In light of the above references and difficulties unique to large scale syntheses of triazine compounds, a few preferred methods of making 2-(2-hydroxyl-4-alkoxyphenyl)-30 4,6-bisaryl-1,3,5-triazine compounds have emerged. These methods, which typically culminate in the alkylation of 2-(2,4-dihydroxyphenyl)-4,6-bisaryl-1,3,5-triazine, have several limitations.

One limitation stems from the fact that 2-(2,4-dihyroxyphenyl)-4,6-bisaryl-1,3,5-triazine has very poor solubility requiring either very high dilution or difficult stirring. On the other hand, in the prior art, 2-chloro-4,6-bisaryl-1,3,5-triazines are first reacted with resorcinol to form 2-(2,4-dihydroxyphenyl)-4,6-bisaryl-1,3,5-5 triazines. Such reaction mixtures are difficult to stir as two immiscible layers are formed, and the lower layer containing the aluminum chloride complexes of the product is generally very thick and tarry sticky mass. Moreover, the isolation of the 2-(2,4-dihydroxyphenyl)-4,6-bisaryl-1,3,5-triazines is not easy due to the poor solubility of such compounds in common organic solvents. An additional drawback is that another step (alkylation step) is needed to make the final product, 2-(2-hydroxy-4-alkoxyphenyl)-4,6-bisaryl-1,3,5-triazines, from 2-(2,4-dihydroxyphenyl)-4,6-bisaryl-15 1,3,5-triazines. The reaction of cyanuric chloride and an aryl compound in the presence of aluminum chloride is typically used to produce 2-(2,4-dihydroxyphenyl)-4,6-bisaryl-1,3,5-triazine.

For some aryl compounds, however, this reaction produces the bisaryl compound in low yield, instead preferring to form either the monoaryl or trisaryl compounds. For example, it has been observed by the inventors that 2-(2-hydroxyl-4-alkoxyphenyl)-4,6-bis(2,4-dimethylphenyl)-1,3,5-triazine is highly reactive under typical reaction conditions, and quickly reacts additional m-xylene, as shown in Scheme II:

SCHEME II

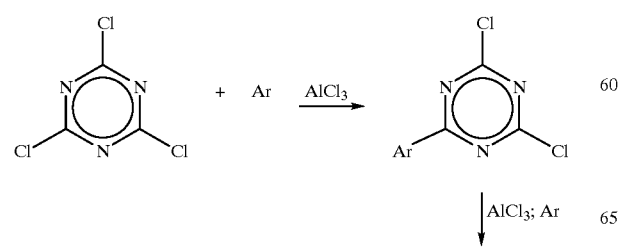

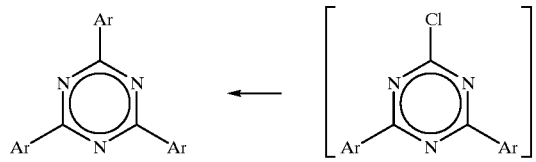

wherein Ar is m-xylene.

Under carefully controlled conditions, and from some aryl groups, this reaction can provide sufficient amounts of certain 2-chloro-4,6-bisaryl-1,3,5-triazine compounds. These may then be reacted with resorcinol in another reaction catalyzed by aluminum chloride to form the corresponding 2-chloro-4,6-bis(2,4-dihydroxyphenyl)-1,3,5-triazine compounds, as shown in Scheme III:

SCHEME III

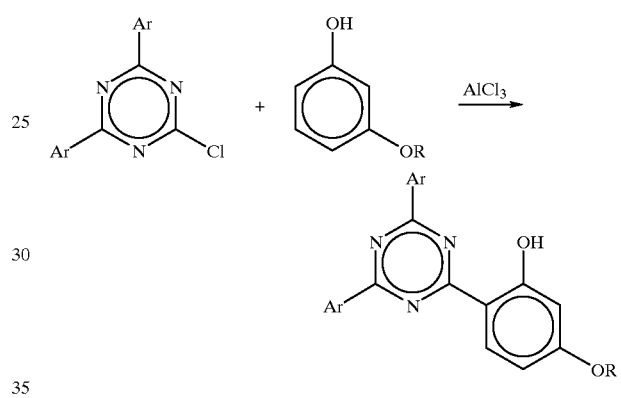

Once the desired 2-(2,4-dihydroxyphenyl)-4,6-bisaryl-1,3,5-triazine compound has been formed, it can then be alkylated to yield the final 2-(2-hydroxy-4-alkoxyphenyl)-4,6-bisaryl-1,3,5-triazine product, as shown in Scheme IV:

SCHEME IV

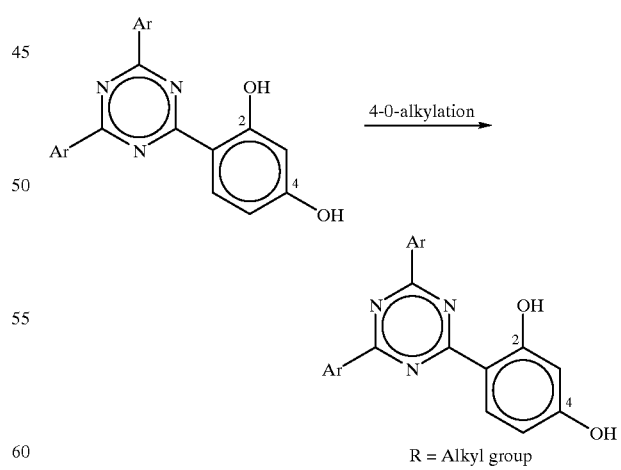

R = Alkyl group

The commercially available UV stabilizer CYASORB® UV-1164 has been made this way by reacting 2-(2,4-dihydroxyphenyl)-4,6-bis(2,4-dimethylphenyl)-1,3,5-triazine with 1-octyl halide in the presence of a base, as shown in Scheme V:

SCHEME V

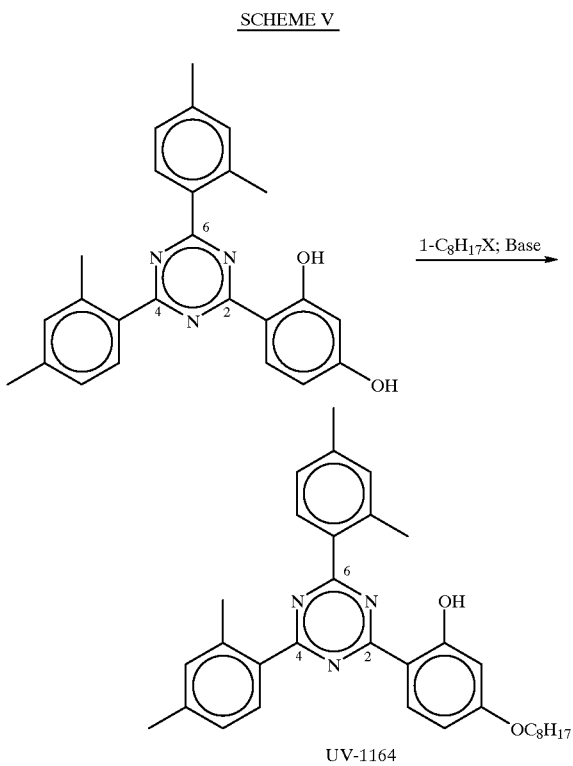

UV-1164

The synthetic process described above can be effective in some cases, yet it has several disadvantages that can render the production of certain UV stabilizers costly and inefficient. For example, this approach is of little use for the production of mixed aryl 2-(2,4-dihydroxyphenyl)-4,6-bisaryl-1,3,5-triazine compounds, since the reaction of cyanuric chloride with a mixture of aryl groups typically forms a mixture of products that are difficult to separate.

As was alluded above, another disadvantage of this process is that the type of aryl group initially reacted with cyanuric chloride can have a dramatic effect on the resulting product mixture. For example, the reaction of xylene and cyanuric chloride in a 2:1 ratio yields a mixture of made up almost exclusively of mono- and tri- substituted xylene triazine compounds. By contrast, the present inventors have discovered that the major product of the reaction of cyanuric chloride with resorcinol is the bis(resorcinol) compound 2-chloro-4,6-bis(2,4-dihydroxyphenyl-1,3–5-triazine. Consequently, variation of the aryl group can lead to unanticipated extraction, separation, and purification problems. These problems render the formation of mixed aryl triazine compounds especially difficult.

These problems are not solved by the aluminum chloride catalyzed reaction of resorcinol and 2,4-bischloro-6-aryl-1,3,5-triazines, as this reaction typically produces an intractable, undesirable reaction mixture. Two immiscible layers are formed upon initiation of the reaction, the lower of which contains aluminum chloride complexes of the products, and is typically a thick, tarry, sticky mass that renders the reaction mixture very difficult to stir. Furthermore, the poor solubilities of the resulting 2,4-hydroxyphenyl triazine compounds hinders their isolation, and leaves comparatively little material for the third step of the reaction.

The present invention avoids the problems described above in part by employing the catalyzed reaction of aryl ethers and halogenated triazine compounds. Many of these reactions are heretofor uncharacterized. For example, the present inventors could not find in the literature a description of the reaction of 3-alkoxyphenol and a 2,4-dichloro-6-aryl-1,3,5-triazine. It was consequently unclear what such a reaction would yield, as shown in Scheme VI:

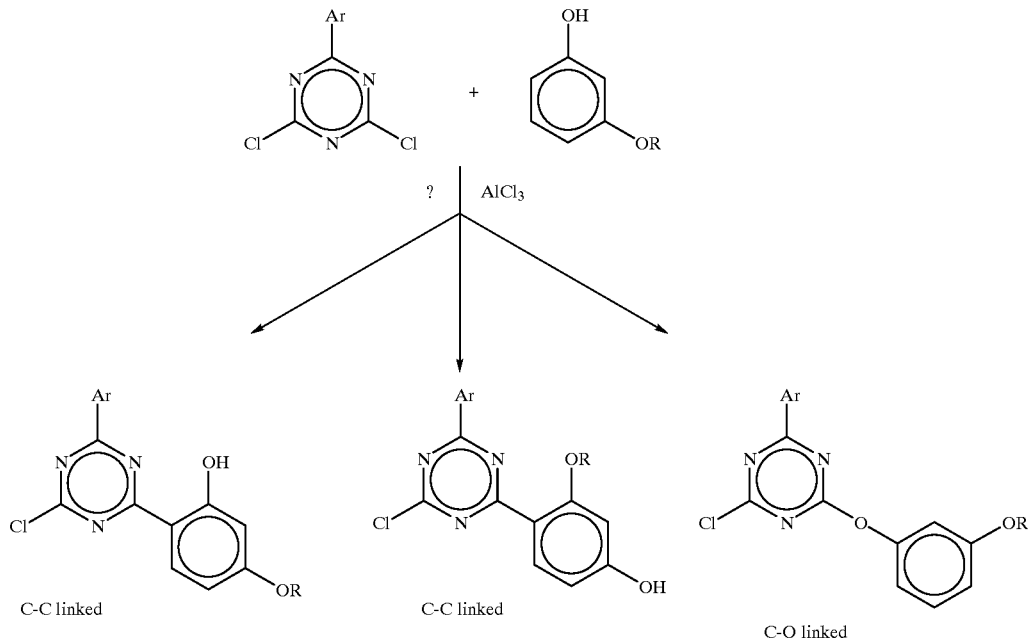

That the reaction of an alkoxyphenol and a substitute triazine could form several different products in an unlimited number of ratios is clear from the literature.

It has been reported that the reaction of cyanuric chloride with phenols can yield both C—C and C—O linked products. See, e.g. Y. Horikoshi et al., *Nippon Kaqaku Kaishi*, 3, (1974) 530–535; CA 81:152177. For example, Japanese Patent 09-059263 describes the formation of C—O linked products from the reaction of cyanuric chloride and substituted pheols, as shown in Scheme VII:

SCHEME VII

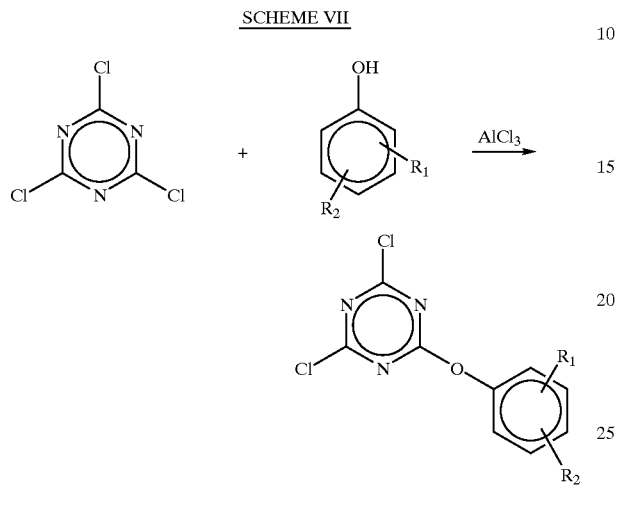

wherein $R_1$ and $R_2$ are H, $C_{1-10}$ alkyl, alkoxy, alkenyl, halo, or nitro.

In light of these references, and as shown in Scheme V above, until now it was unclear weather the reaction of cyanuric chloride and 3-alkoxyphenol would yield C—C or C—O linked products. Furthermore, the regiochemistry of the preferred products of the reaction was also unknown, as was whether the reaction would allow the selective monosubstitution of chlorotriazine. By studying this reaction, the present inventors have surprisingly found a particularly effective means of synthesizing triazine compounds suitable as UV stabilizers.

SUMMARY OF THE INVENTION

The object of the present invention is a process for preparing a triazine compound of Formula A.

FORMULA A

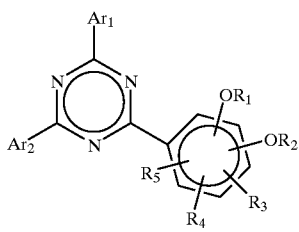

$Ar_1$ and $Ar_2$ in Formula A may be the same or different and each is a deprotonated radical of a compound of Formula B.

FORMULA B

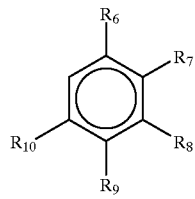

The groups $R_1$, $R_2$, $R_3$, $R_4$, $R_5$, $R_6$, $R_7$, $R_8$, $R_9$, and $R_{10}$ in a compound of Formula B may be the same or different and each is hydrogen, alkyl of 1 to 24 carbon atoms, cycloalkyl of 5 to 24 carbon atoms, aralkyl of 7 to 24 carbon atoms, alkoxy, amine, thiol, and $R_6$, and $R_7$ taken together, $R_7$ and $R_8$ taken together, $R_8$ and $R_9$ taken together, or $R_9$ and $R_{10}$ taken together may be part of a fused carbocyclic ring optionally containing O, N, or S atoms. The process comprises reacting in the presence of a catalyst a compound of Formula C:

FORMULA C

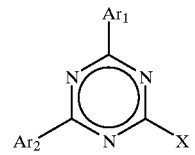

wherein X is a halogen with a compound of Formula D:

FORMULA D

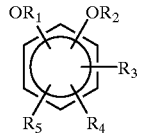

at a suitable temperature and pressure and for a time sufficient to produce the compound of Formula A.

DETAILED DESCRIPTION OF THE INVENTION $Ar_1$ and $Ar_2$ in the present disclosure is understood to include a carbon structure of 1 to 24 carbons wherein $R_1$, $R_2$, $R_3$, $R_4$, $R_5$, $R_6$, $R_7$, $R_8$, $R_9$, and $R_{10}$ are the same or different and each is hydrogen, alkyl of 1 to 24 carbon atoms, cycloalkyl of 5 to 24 carbon atoms, aralkyl of 7 to 24 carbon atoms, alkoxy, amine, and thiol. $R_6$ and $R_7$ may be taken together, $R_8$ and $R_9$ may be taken together, or $R_9$ and $R_{10}$ may be taken together. An example of $Ar_1$ and $Ar_2$ may be substituted phenyl, biphenyl, naphthyl, wherein the aryl group is substituted at least once by a R group comprises an alkyl group such as methyl, ethyl, propyl, butyl, pentyl, hexyl, septyl, octyl, nonyl, decyl, saturated or unsaturated in straight chain, branched, or cyclic form, an hydroxyl, an ether —OR, amine —NHR, $NR_2$, or —NRR' or thiol —SR. Furthermore, the R or R' group may be substituted with at least one additional group, such group including hydroxy, alkyl straight chain or branched, alkoxy (e.g. methoxy, n-butoxy, 2-ethylhexyloxy and n-octyloxy), sulfonic, halide (e.g., iodo, bromo, chloro, fluoro), haloalkyl (e.g. dicholoromethyl and trifluoromethyl). The list is not intended to be all encompassing, simply demonstrative.

Formula B in the present disclosure is understood to include substituted phenol wherein the substitution group may be in any position on the ring. The alkoxy group includes but is not limited to an ether of formula —OR, wherein the R group comprises an alkyl group such as methyl, ethyl, propyl, butyl, pentyl, hexyl, septyl, octyl, nonyl, decyl, saturated or unsaturated, in straight chain, branched, or cyclic form. Furthermore, the R group may be substituted with at least one additional group, such group including hydroxy, alkyl saturated or unsaturated, in straight chain, branched, or cyclic form, alkoxy (e.g. methoxy, n-butoxy, 2-ethylhexyloxy and n-octyloxy), sulfonic, halide (e.g., iodo, bromo, chloro, fluoro), haloalkyl (e.g. dicholoromethyl and trifluoromethyl). The list is not intended to be all encompassing, simply demonstrative.

The Lewis acid catalyst should be present in a sufficient amount to react with the number of halogens being substituted. Lewis acid includes but is not limited to $AlCl_3$, $AlBr_3$, or any other Lewis acid suitable for a Friedels-Craft reaction. The list is not intended to be all encompassing, simply demonstrative. The preferred Lewis acid is aluminum chloride. Based on the amount of 2-chloro-4,6-bisaryl-1,3,5-triazine, the preferred amount of Lewis acid is between about 0.5 mol to about 5 mol equivalents to each chloride present in the precursor chlorotriazine compound.

The aromatic solvent used in the reaction includes but is not limited to halogenated benzene such as chlorobenzne, dichlorobenzene, trichlorobenzene, 1,1,2,2-tetrachloroethane, bromobenzene, dibromobenzene, tribromobenzene, etc., toluene, dimethylbenzene, trimethylbenzene, in any substitution pattern, nitrobenzene, anisole, or mixtures of these with one another. This list is not intended to be all encompassing, simply demonstrative.

The present inventors unexpectedly discovered that under certain conditions 2-(2-hydroxy-4-alkyloxyphenyl)-4,6-bisaryl-1,3,5-triazine compounds are formed in a one-pot process from the corresponding 2-chloro-4,6-bisaryl-1,3,5-triazine compounds.

The aryl groups indicated by $Ar_1$ and $Ar_2$ may be substituted or unsubstituted aryl groups, including but not limited to phenyl, alkylphenyl, alkoxyphenyl, halophenyl, alkoxyhalophenyl, aminophenyl, biphenyl, substituted biphenyl, naphthalene, teralin, substituted naphthalenes and tetralins, or any oxy, alkoxy, nitro, amide, amine, thiol, alkylthiol, or halogen derivatives thereof. The aryl groups $Ar_1$ and $Ar_2$ should be in sufficient amount to react with the 2-chloro-4,6-bisaryl-1,3,5-triazines to produce a 2-(2-hydroxy-4-alkoxyphenyl)-4,6-bisaryl-1,3,5-triazines. Preferably the amount should be between about 0.8 mol to about 2 mol equivalents based on the amount of chlorides present in the precursor chlorotriazine.

The temperature range for the reaction is between about 0° C. to about 150° C. Preferably, between about 30° C. to about 80° C. The reaction time for the addition of 2-alkoxyphenol is between about 1 hour to about 50 hours. Preferably, between about 2 hours to about 12 hours.

Additional features of the present invention will be apparent from the claims and the non-limiting examples.

EXAMPLES

Examples and reaction schemes for producing specific examples of substituted triazines in accordance with the invention are provided below. While the following examples illustrate preparations with one or more substituted aryl ring, one of ordinary skill will understand that these reactions may also be carried out with any of a variety of other substituted aryl rings, where when necessary, reactive substituents on such other substituted aryl rings are protected in accordance with procedures and reagents well known and understood by those of ordinary skill.

Example 1

Reaction of 2-chloro-4,6-bis(2,4-dimethylphenyl)-1,3,5-triazine (1) with 3-methoxyphenol (2); Preparation of 2-(2-hydroxy-4-methoxy)-4,6-bis(2,4-dimethylphenyl-1,3,5-triazine (3)

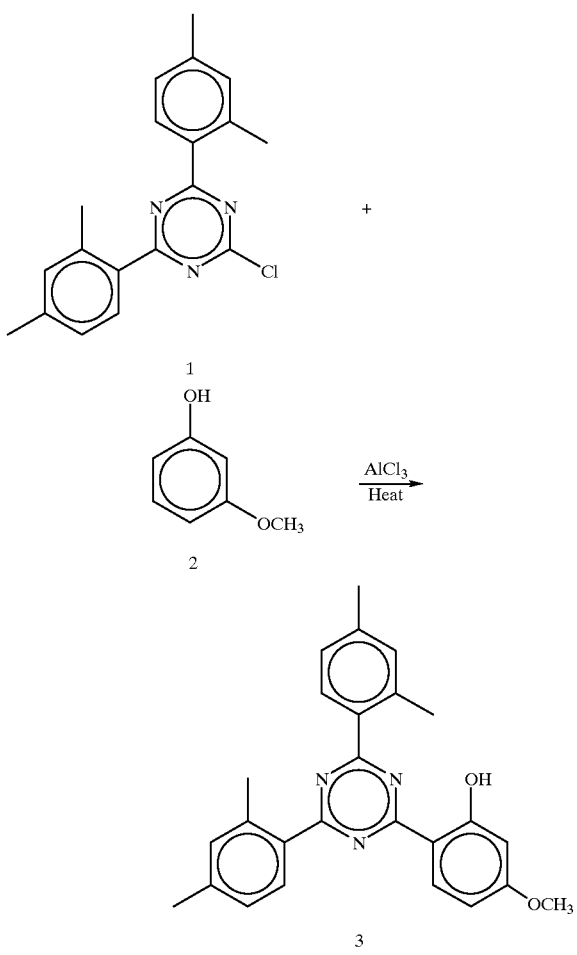

To a stirred mixture of 2-chloro-4,6-bis(2,4-dimethylphenyl)-1,3,5-triazine (3.24 g, 10 mmol) 1 and 3-methoxyphenol (1.86 g) 2 in 25 mL of chlorobenzene at room temperature under nitrogen was added 1.33 g of aluminum trichloride. The mixture was heated to 60° C. for 4 hr. The reaction mixture was slowly poured into a vigorously stirred mixture of 100 mL 5% aq. hydrochloric acid, ice, and water (total volume 300 mL). A precipitate formed, was collected, washed with water, and dried in vacuo at 40° C. overnight. The formation of compound 3 was confirmed by thermal spray MS ($MH^+$m/e=412) and UV spectroscopy ($\lambda$=298, 342 nm).

Example 2

Reaction of 2-chloro-4,6-bis(2,4-dimethylphenyl)-1.3,5-triazine (1) with 1,3-dioctyloxybenzene (4): Preparation of 2-(2-hydroxy-4-octyloxy)-4,6,-bis(2,4-dimethylphenyl)-1,3,5-triazine. (5)

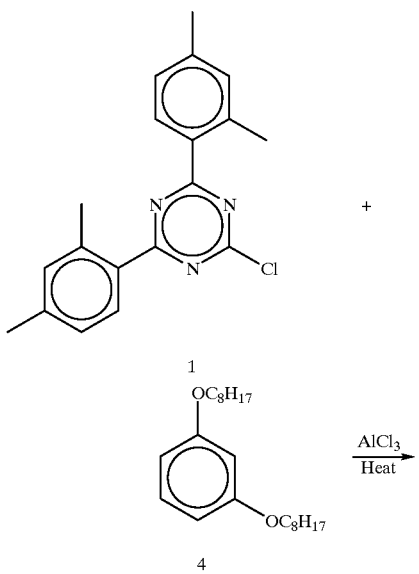

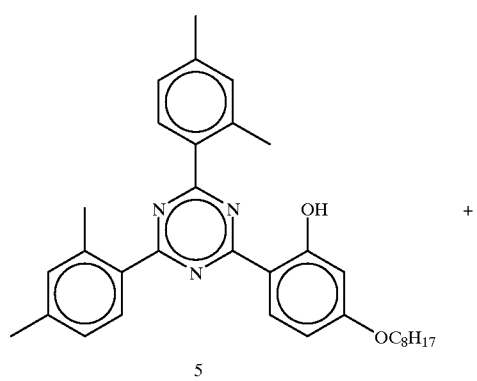

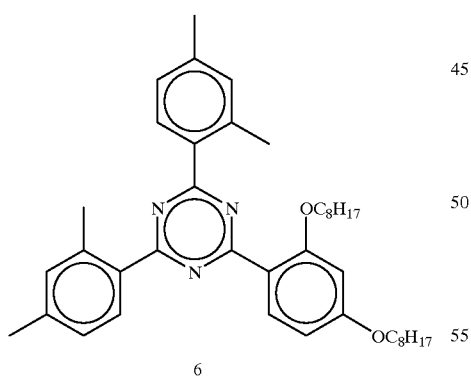

To a stirring mixture of 2-chloro-4,6-bis(2,4-dimethylphenyl)-1,3,5-triazine (3.23 g) 1 and 1,3-dioctyloxybenzene (3.34 g) 4 in 25 mL of chlorobenzene was added aluminum chloride (1.6 g) at room temperature. The reaction mixture was stirred at room temperature for 2 hr and then gradually heated to 85° C. for 2.5 hr. The heating was discontinued and the reaction mixture was stirred at room temperature for 20 hr. The reaction mixture was treated with aqueous 3% HCl. The mixture was then extracted with methylene chloride, and the organic layer was washed with water, dried over anhydrous sodium sulfate and concentrated under reduced pressure. The product obtained was analyzed by TLC, HPLC, and LCMS with yielded both 2-(2-hydroxy-4-octyloxy)-4,6-bis(2,4-dimethylphenyl)-1,3,5-triazine 5 and 2-(2,4-dioctyloxy)-4,6-bis(2,4-dimethylphenyl)-1,3,5-triazine 6 as the main products.

What is claimed is:

1. A process for preparing a triazine compound of Formula A

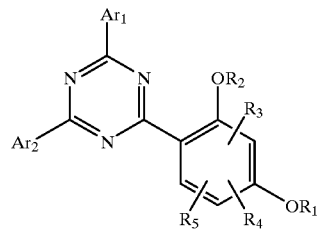

wherein $Ar_1$ and $Ar2$ are the same or different and each is a radical of a compound of Formula B

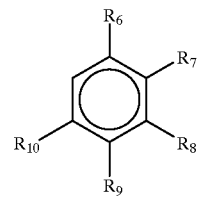

wherein $R_1$, $R_6$, $R_8$ are the same or different and each is alkyl of 1 to 24 carbon atoms, cycloalkyl of 5 to 24 carbon atoms, aralkyl of 7 to 24 carbon atoms, $R_2$ is hydrogen, $R_3$, $R_4$, $R_5$, $R_7$, $R_9$, and $R_{10}$ are the same or different and each is hydrogen, alkyl of 1 to 24 carbon atoms, cycloalkyl of 5 to 24 carbon atoms, aralkyl of 7 to 24 carbon atoms, and $R_6$ and $R_7$ taken together, R7 and $R_8$ taken together, $R_8$ and $R_9$ taken together, or $R_9$ and $R_{10}$ taken together may be part of a fused carbocyclic ring optionally containing O, N, or S atoms, which process comprises:

reacting in the presence of a first catalyst a compound of Formula C:

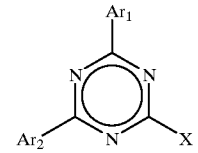

wherein X is a halogen with a compound of Formula D:

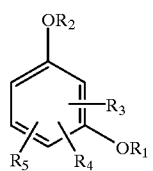

Formula D at a temperature from about 0° C. to about 150° C. and a suitable pressure, in the presence of a solvent and for a time from about 1 hour to about 40 hours to produce the compound of Formula A.

2. The process of claim 1, which further comprises an initial step of reacting cyanuric halide with a compound of Formula B at a temperature from about 0° C. to about 150° C. and a suitable pressure in the presence of a solvent and a second catalyst and for a time sufficient to produce the compound of Formula C prior to reacting said compound with the compound of Formula D.

3. The process of claim 2, wherein the compound of Formula C is not isolated prior to reacting with the compound of Formula D.

4. The process according to claim 1, wherein the temperature for the addition of the compound of Formula D is between about 30° C. to about 80° C.

5. The process according to claim 1, wherein the suitable solvent is an inert aromatic solvent.

6. The process according to claim 5, wherein said inert solvent is chosen from one of the following chlorobenzene, dichlorobenzene, trichlorobenzene, bromobenzene, dibromobenzene, tribromobenzene, toluene, xylene, trimethylbenzene, nitrobenzene, and anisole.

7. The process according to claim 1, wherein the catalyst is a Lewis acid.

8. The process according to claim 7, wherein said Lewis acid is an aluminum trihalide, zinc dihalide, boron trihalide, titanium tetrahalide, or tin tetrahalide.

9. The process according to claim 6, wherein the mol ratio of compound of Formula C to catalyst is between about 0.5 to about 5.

10. The process according to claim 1, wherein the reaction time is between about 2 hours and about 12 hours.

11. The process of claim 1, wherein the mol ratio of the compound of Formula D to the compound of Formula C is a range of between about 0.8 to about 2.

12. The process according to claim 8, wherein the Lewis acid is aluminum trichloride or aluminum tribromide.

* * * * *